(12) United States Patent
Dierking et al.

(10) Patent No.: US 10,363,154 B2
(45) Date of Patent: *Jul. 30, 2019

(54) STENT DESIGNS FOR USE WITH ONE OR MORE TRIGGER WIRES

(71) Applicant: Cook Medical Technologies LLC, Bloomington, IN (US)

(72) Inventors: William K. Dierking, Louisville, KY (US); David Ernest Hartley, Wannanup (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/814,952

(22) Filed: Nov. 16, 2017

(65) Prior Publication Data

US 2018/0071122 A1    Mar. 15, 2018

Related U.S. Application Data

(63) Continuation of application No. 13/429,983, filed on Mar. 26, 2012, now Pat. No. 9,833,345, which is a
(Continued)

(51) Int. Cl.
*A61F 2/82* (2013.01)
*A61F 2/07* (2013.01)
(Continued)

(52) U.S. Cl.
CPC .................. *A61F 2/95* (2013.01); *A61F 2/91* (2013.01); *A61F 2002/8486* (2013.01);
(Continued)

(58) Field of Classification Search
CPC ........ A61F 2/07; A61F 2/2418; A61F 2/2427; A61F 2220/0075; A61F 2/86; A61F 2/915; A61F 2250/0098
See application file for complete search history.

(56) References Cited

U.S. PATENT DOCUMENTS 5,383,887 A    1/1995  Nadal
5,527,355 A    6/1996  Ahn
(Continued)

FOREIGN PATENT DOCUMENTS

DE    202007005491    7/2007
JP    2008-091699     4/2008

OTHER PUBLICATIONS

International Search Report dated Aug. 4, 2009 for PCT/US2009/00074; 3 pgs.
(Continued)

*Primary Examiner* — Ann Schillinger
(74) *Attorney, Agent, or Firm* — Brinks Gilson & Lione (57) ABSTRACT

The present embodiments provide a stent for use in a medical procedure that comprises a series of proximal apices disposed at a proximal end of the stent and a series of distal apices disposed at a distal end of the stent. A trigger wire is adapted to be coupled to at least one of the proximal apices to restrain a proximal end of the stent during delivery. In a first embodiment, a first proximal apex comprises a bore for receiving the trigger wire, and a second proximal apex, disposed adjacent to the first proximal apex, comprises at least one barb. The trigger wire therefore is only coupled to selected ones of the proximal apices. In an alternative embodiment, a first proximal apex comprises a first bore and a second, adjacent proximal apex comprises a second bore, such that a single trigger wire may be disposed through the first and second bores to restrain the first and second proximal apices during delivery.

17 Claims, 5 Drawing Sheets

Related U.S. Application Data continuation of application No. 12/364,162, filed on Feb. 2, 2009, now Pat. No. 8,163,007.

(60) Provisional application No. 61/027,192, filed on Feb. 8, 2008.

(51) Int. Cl.
*A61F 2/95* (2013.01)
*A61F 2/91* (2013.01)
*A61F 2/848* (2013.01)
*A61F 2/966* (2013.01)

(52) U.S. Cl.
CPC ............... *A61F 2002/9505* (2013.01); *A61F 2002/9511* (2013.01); *A61F 2002/9665* (2013.01); *A61F 2220/0016* (2013.01); *A61F 2220/0075* (2013.01); *A61F 2230/0013* (2013.01); *A61F 2250/0063* (2013.01)

(56) References Cited

U.S. PATENT DOCUMENTS

| | | | |
|---|---|---|---|
| 5,562,728 A | 10/1996 | Lazarus et al. | |
| 5,843,170 A | 12/1998 | Ahn | |
| 6,210,435 B1 | 4/2001 | Piplani et al. | |
| 6,221,102 B1 | 4/2001 | Baker et al. | |
| 6,287,330 B1 * | 9/2001 | Johansson | A61F 2/07 606/194 |
| 6,322,587 B1 | 11/2001 | Quiachon et al. | |
| 6,361,556 B1 | 3/2002 | Chuter | |
| 6,395,022 B1 | 5/2002 | Piplani et al. | |
| 6,454,796 B1 | 9/2002 | Barkman | |
| 6,652,580 B1 | 11/2003 | Chuter et al. | |
| 6,682,557 B1 | 1/2004 | Quiachon et al. | |
| 6,808,534 B1 | 10/2004 | Escano | |
| 6,814,748 B1 | 11/2004 | Baker et al. | |
| 6,849,087 B1 | 2/2005 | Chuter | |
| 7,122,058 B2 | 10/2006 | Levine et al. | |
| 7,166,125 B1 | 1/2007 | Baker et al. | |
| 7,527,645 B2 | 5/2009 | Perez et al. | |
| 7,591,843 B1 | 9/2009 | Escano et al. | |
| 7,708,771 B2 | 5/2010 | Chuter et al. | |
| 7,947,075 B2 | 5/2011 | Goetz et al. | |
| 7,998,194 B2 | 8/2011 | Pollock et al. | |
| 8,163,007 B2 | 4/2012 | Dierking et al. | |
| 8,840,659 B2 * | 9/2014 | Roeder | A61F 2/07 623/1.36 |
| 9,060,853 B2 * | 6/2015 | Roeder | A61F 2/07 |
| 2004/0220655 A1 | 11/2004 | Swanson et al. | |
| 2005/0060018 A1 | 3/2005 | Dittman | |
| 2005/0125020 A1 | 6/2005 | Meade et al. | |
| 2005/0137701 A1 | 6/2005 | Salahieh et al. | |
| 2005/0149166 A1 * | 7/2005 | Schaeffer | A61F 2/07 623/1.13 |
| 2006/0004433 A1 | 1/2006 | Greenberg et al. | |
| 2007/0270938 A1 | 11/2007 | Osypka | |
| 2008/0027529 A1 | 1/2008 | Hartley et al. | |
| 2008/0051875 A1 | 2/2008 | Cottone et al. | |
| 2009/0030497 A1 | 1/2009 | Metcalf et al. | |
| 2009/0082845 A1 | 3/2009 | Chobotov | |
| 2009/0125096 A1 | 5/2009 | Chu et al. | |
| 2009/0171442 A1 | 7/2009 | Young et al. | |
| 2009/0234429 A1 | 9/2009 | Lau | |
| 2009/0299462 A1 | 12/2009 | Fawzi et al. | |
| 2010/0010622 A1 | 1/2010 | Lowe et al. | |
| 2010/0161028 A1 | 6/2010 | Chuter et al. | |

OTHER PUBLICATIONS

International Preliminary Report on Patentability completed Jun. 18, 2010 for PCT/US2009/00074; 13 pgs.
Written Opinion completed dated Aug. 4, 2009 for PCT/US2009/00074; 6 pgs.
Office Action dated Jul. 17, 2013 for Japanese Patent Application JP2010-545876, 9 pgs. including English translation.
Examination Report No. 1 for Australian Patent Application 2009210732 dated Nov. 29, 2012, 2 pgs.
Office Action for Canadian Patent Application 2711849 dated Jul. 15, 2014, 3 pgs.

* cited by examiner

STENT DESIGNS FOR USE WITH ONE OR MORE TRIGGER WIRES

RELATED APPLICATIONS

This application is a continuation of U.S. application Ser. No. 13/429,983, filed Mar. 26, 2012, which is a continuation of U.S. application Ser. No. 12/364,162, filed Feb. 2, 2009, now U.S. Pat. No. 8,163,007, which claims the benefit of the filing date under 35 U.S.C. § 119(e) of Provisional U.S. Application Ser. No. 61/027,192, entitled "Stent Designs For Use With One or More Trigger Wires," filed Feb. 8, 2008, which are all incorporated by reference herein in their entireties.

BACKGROUND

The present invention relates generally to apparatus and methods for treating medical conditions, and more specifically, to stents for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires.

In view of the above, it would be desirable to provide a stent that may be compressed to a reduced diameter delivery profile, while improving the trigger wire attachment to the stent and reducing the likelihood of barb entanglement and damage to the trigger wires and stent struts.

SUMMARY

The present embodiments provide a stent for use in a medical procedure that comprises a series of proximal apices disposed at a proximal end of the stent and a series of distal apices disposed at a distal end of the stent. A trigger wire is adapted to be coupled to at least one of the proximal apices to restrain a proximal end of the stent during delivery, preferably in a manner that may reduce barb entanglement and also may reduce the likelihood of damage to the trigger wire and/or the stent itself.

In one example, the stent comprises a series of proximal apices, a series of distal apices, and at least one strut segment disposed between a proximal apex and a distal apex. The strut segment enables expansion of the stent from a compressed state to a deployed state. The series of proximal apices may comprise alternating first and second proximal apices having different characteristics. For example, a first proximal apex may comprise a bore for receiving a trigger wire, and a second proximal apex, disposed adjacent to the first proximal apex, may comprise at least one barb for engaging tissue. A trigger wire therefore may be looped through only selected ones of the proximal apices, such as every first proximal apex, during delivery of the stent, such that the second proximal apices are not restrained by trigger wires. Due to the stent configuration, one or more of the first proximal apices are directly restrained using trigger wires, and the second proximal apices also are pulled inward indirectly due to the restraint of the adjacent first proximal apices.

In another example, the stent comprises a first proximal apex comprising a first bore and a second proximal apex comprising a second bore. A single trigger wire may be disposed through the first and second bores to restrain the first and second proximal apices during delivery. With this configuration, the second proximal apex may comprise first and second regions. At least one integral barb may be formed in the first region, and the second bore may be formed in the second region. A recessed portion may be formed in the second proximal apex at a location distal to the second bore. When the single trigger wire is disposed through the first and second bores during delivery of the stent, the first bore of the first proximal apex may be pulled towards the second bore of the second proximal apex such that the first and second bores are disposed substantially in longitudinal alignment with one another. At this time, the first proximal apex may become substantially nested within the recessed portion of the second proximal apex during delivery.

The distal apices of the aforementioned stents may comprise a suture bore adapted to receive a suture for coupling the distal end of the stent to a graft material. Further, each of the distal apices may comprise an imaging bore adapted to receive a radiopaque marker. The imaging bore may be disposed proximal to the suture bore, such that the imaging bore is adapted to be aligned with a proximal edge of the graft material. Additionally, at least one barb may be integrally formed in an end region of each of the distal apices.

Advantageously, the stents described herein may reduce the number of trigger wires required during delivery, for example, since a single trigger wire is not needed to restrain each individual apex. Moreover, barb entanglement may be reduced during delivery of the stent, particularly since barbs are not disposed on each proximal apex of the stent. Further, since the trigger wires are disposed only through bores in one or more of the proximal apices, as opposed to being disposed through vertices associated with the stent struts, damage to the trigger wires and/or stent struts may be reduced, particularly when the stent is in a compressed delivery state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
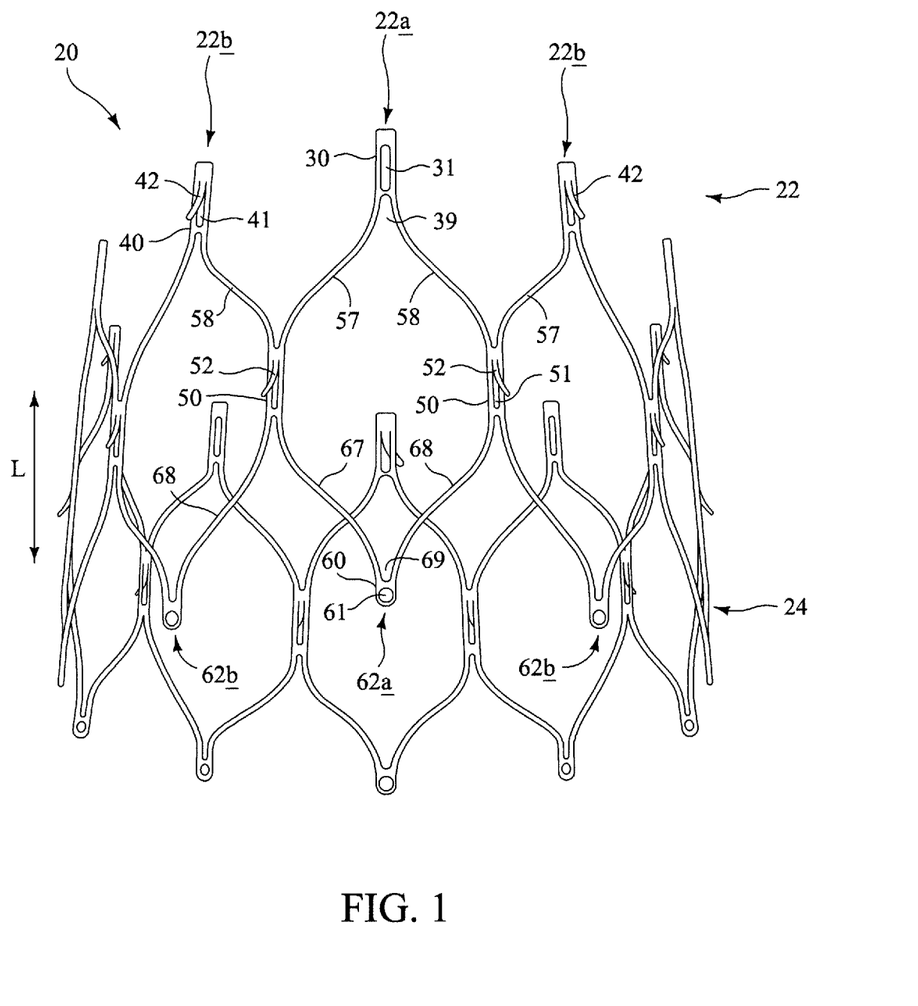
FIG. 1 is a lower perspective view of an exemplary cannula-cut stent.

Referring to FIG. 1, a stent 20 may be manufactured from a continuous cylinder into which a pattern may be cut by a laser or by chemical etching to produce slits in the wall of the cylinder. The resulting structure may then be heat set to give it a desired final configuration. The preferred final configuration includes a shape having a series of proximal apices and a series of distal apices, as generally shown in FIG. 1. Therefore, the proximal end 22 of the stent 20 may comprise multiple adjacent proximal apices 22a and 22b, while the distal end 24 of the stent 20 may comprise multiple adjacent distal apices 62a and 62b, as shown in FIG. 1.

In previously-known stents, one or more trigger wires may have been disposed through a vertex 39 at the proximal end 22 and/or through a vertex 69 at the distal end 24 of the stent. When the stent is compressed for delivery, if a trigger wire was disposed through the vertices 39 and 69, the trigger wire may become pinched against the struts of the stent, which may damage the stent struts and/or the trigger wire itself. As explained below, the present embodiments utilize a different approach to coupling one or more trigger wires to the stent 20.

Figure 2:
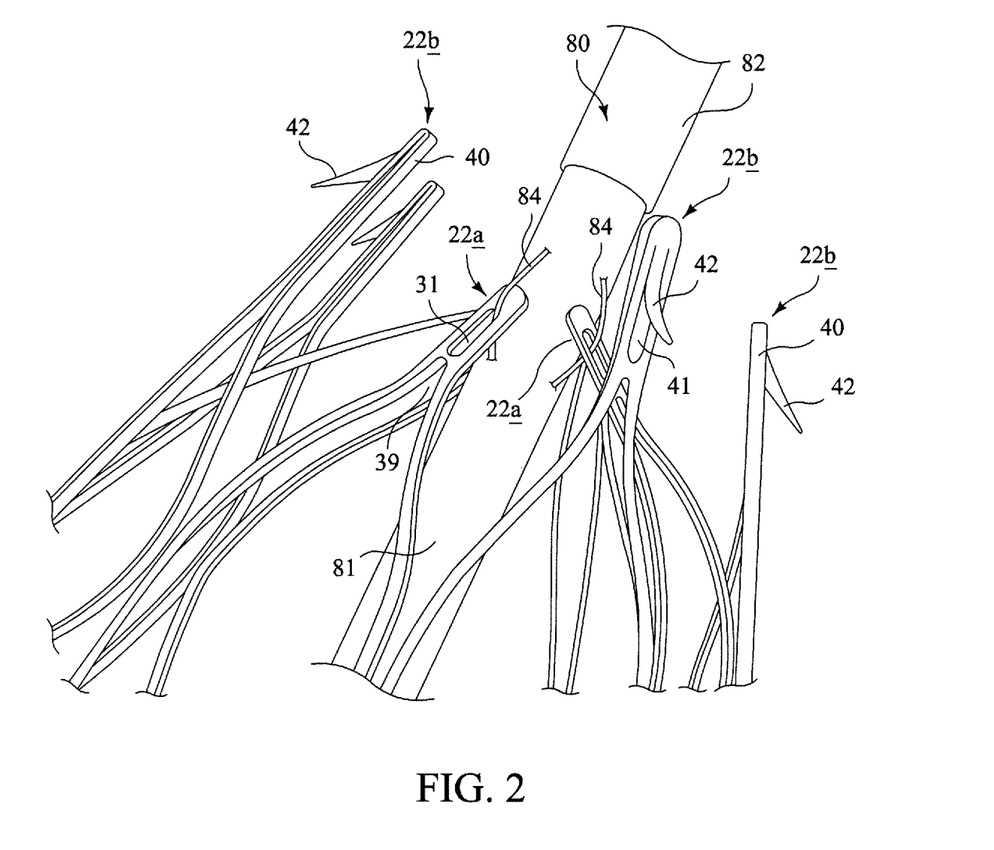
FIG. 2 is a perspective view illustrating the attachment of the stent of FIG. 1 to a delivery system.

Referring still to FIGS. 1-2, at least one pair of adjacent, proximal apices 22a and 22b comprises different features. For example, as shown in FIG. 2, a first proximal apex 22a may comprise an end region 30 having a bore 31 formed therein, wherein the bore 31 is configured to receive a trigger wire 84. A second, adjacent proximal apex 22b comprises an end region 40 having an integral barb 42 formed therein, as shown in FIGS. 1-2. However, the second proximal apex 22b is not configured to be restrained using a trigger wire, as explained and shown in FIG. 2 below. By using adjacent proximal apices 22a and 22b having the different features shown herein, an improved trigger wire attachment may be achieved and barb entanglement may be reduced, as explained further below.

As noted above, the stent 20 may comprise one or more barbs 42 disposed in at least one of the end regions 40 of the second proximal apices 22b. The barbs 42 may be formed by laser cutting a desired barb shape into the end regions 40. A slit 41 therefore is formed into each end region 40 after the desired barb shape is formed, as shown in FIGS. 1-2. Once the desired barb shape is cut, a main body of the barb 42 may be bent in a radially outward direction with respect to the end region 40. The angle may comprise any acute angle, or alternatively may be substantially orthogonal or obtuse. If desired, the barbs 42 may be sharpened, for example, by grinding the tip of the barb, to facilitate engagement at a target tissue site.

Referring still to FIG. 1, the stent 20 may comprise at least one strut segment disposed between the proximal and distal apices. For example, multiple angled strut segments may be disposed between a first proximal apex 22a and a corresponding distal apex 62a, and an identical set of angled strut segments may be disposed between an adjacent, second proximal apex 22b and a corresponding distal apex 62b. By way of example, the first proximal apex 22a extends distally and splits into first and second angled strut segments 57 and 58, respectively, thereby forming a proximal vertex 39, as shown in FIG. 1. In a compressed state, the first and second angled strut segments 57 and 58 may be compressed such that they are substantially parallel to one another. In the expanded state shown in FIG. 1, the first and second angled strut segments 57 and 58 are disposed an angle relative to a longitudinal axis L of the stent 20. In the expanded state, the first and second angled strut segments 57 and 58 may be disposed at an angle of about 20-60 degrees relative to the longitudinal axis L of the stent 20, as depicted in FIG. 1.

Similarly, each distal apex 62a may extend in a proximal direction and splits into first and second angled strut segments 67 and 68, respectively, thereby forming a distal vertex 69. The first angled strut segments 57 and 67 of the proximal and distal apices 22a and 62a, respectively, may meet with the second angled strut segments 58 and 68 of the adjacent proximal and distal apices 22b and 62b, respectively, thereby forming a transition region 50. In this manner, the stent 20 may be formed into a continuous, generally cylindrical shape, as shown in FIG. 1.

Expansion of the stent 20 is at least partly provided by the angled strut segments 57, 58, 67 and 68, which may be substantially parallel to one another in a compressed state, but may tend to bow outward away from one another in the expanded state shown in FIG. 1. As explained further below, the stent 20 may be formed from any suitable material, and preferably a laser-cut nitinol cannula. If manufactured from nitinol, the stent 20 may assume the expanded state shown in FIG. 1 upon removal of a delivery sheath.

Each transition region 50 may be oriented in a direction that is substantially parallel to the longitudinal axis L of the stent 20, as shown in FIG. 1. Further, each transition region 50 may comprise a larger surface area relative to the angled segments, since the transition regions are composed substantially of multiple different angled segments 57, 58, 67 and 68 meeting up at a central location.

Referring still to FIG. 1, the stent 20 may comprise at least one barb 52 disposed in at least one of the transition regions 50. The barb 52 may be formed integrally, as part of the strut, or may comprise an external barb that is adhered to a surface of the transition regions 50. Preferably, as shown in FIG. 1, multiple integral barbs 52 are provided. The barbs 52 may be formed by laser cutting a desired barb shape into the transition regions 50. In this manner, the barbs are monolithic with the transition region 50. A slit 51 therefore is formed into the transition region 50 after the desired barb shape is formed, as shown in FIG. 1. Since the transition regions 50 may comprise an increased surface area relative to other regions of the stent 20, it may be easier to perforate portions of the transition regions 50 without adversely affecting the structural integrity of the stent. Once the desired barb shape is cut, a main body of the barb 52 may be bent in an outward direction at any angle with respect to the transition region 50 and optionally may be sharpened to facilitate engagement at a target tissue site.

Each of distal apices 62a and 62b may comprise an end region 60 having a bore 61 formed therein, as shown in FIG. 1. The distal end 24 of the stent 20 may be coupled to a proximal end of graft material (not shown). The distal apices 62a and 62b may be coupled to the graft material, for example, using one or more sutures that are looped through the graft material and the bores 61 of the stent 20. In this manner, the stent 20 may be used as an attachment stent for endovascular graft fixation. For example, the graft material may overlap with an aneurysm to seal off fluid flow into the aneurysm, while the proximal end 22 of the stent 20 may extend in a proximal direction away from the graft material, e.g., to engage a healthy portion of a vessel wall away from a diseased portion of the aneurysm.

The stent 20 has a reduced diameter delivery state so that it may be advanced to a target location within a vessel or duct. The stent 20 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 20. Further, the struts of the stent 20 may comprise a substantially flat wire profile or may comprise a rounded profile. As best seen in FIG. 2, the struts of the stent 20 generally comprise a flat wire profile.

The stent 20 may be manufactured from a super-elastic material. Solely by way of example, the super-elastic material may comprise a shape-memory alloy, such as a nickel titanium alloy (nitinol). If the stent 20 comprises a self-expanding material such as nitinol, the stent may be heat-set into the desired expanded state, whereby the stent 20 can assume a relaxed configuration in which it assumes the preconfigured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Referring now to FIG. 2, the stent 20 may be delivered to a target site in a compressed configuration using a pushing member 80 and a plurality of trigger wires 84. In FIG. 2, the exemplary pushing member 80 comprises a main body 81 and a tapered region 82, which is disposed proximal to the main body 81. The tapered region 82 may subsequently transition into a smaller diameter at a proximal location, such that the relatively small diameter proximal region allows for atraumatic access and delivery. The plurality of trigger wires 84 may be disposed within the confines of the main body 81, and may span the length of the pushing member 80. The triggers wires 84 also may be activated by manipulating one or more handles, with optional locking features, to control deployment of the proximal end 22 of the stent 20.

A single trigger wire 84 may be looped through the bore 31 of selected ones of the first proximal apices 22a to restrain the stent 20 during delivery. Trigger wires are not coupled to the second proximal apices 22b, which comprise the barbs 42. In the embodiment shown, the trigger wires 84 are only disposed through alternating proximal apices, as seen in FIG. 2. By restraining selected ones of the first proximal apices, such as each first proximal apex 22a, the adjacent second proximal apices 22b also may be indirectly pulled in a radially inward direction during delivery. The configuration of the stent 20, and in particular the angled segments 57, 58, 67 and 68 that meet up at transition regions 50, facilitates the indirect compression of the adjacent second proximal apices 22b. Advantageously, since only selected ones of the proximal apices are restrained during delivery, the number of trigger wires may be reduced. Moreover, since the barbs 42 are only disposed on every other apex, barb entanglement may be reduced or eliminated, as depicted in FIG. 2.

Another advantage associated with the design of the stent 20 is that the trigger wires 84 are only disposed through the bores 31 of the first proximal apices 22a, as opposed to being disposed through the vertices 39. Therefore, the trigger wires 84 may be less likely to become damaged during compression of the stent 20. Further, the stent struts themselves are less likely to become damaged since the trigger wires 84 are isolated within the bores 31 of the first proximal apices 22a.

Figure 3:
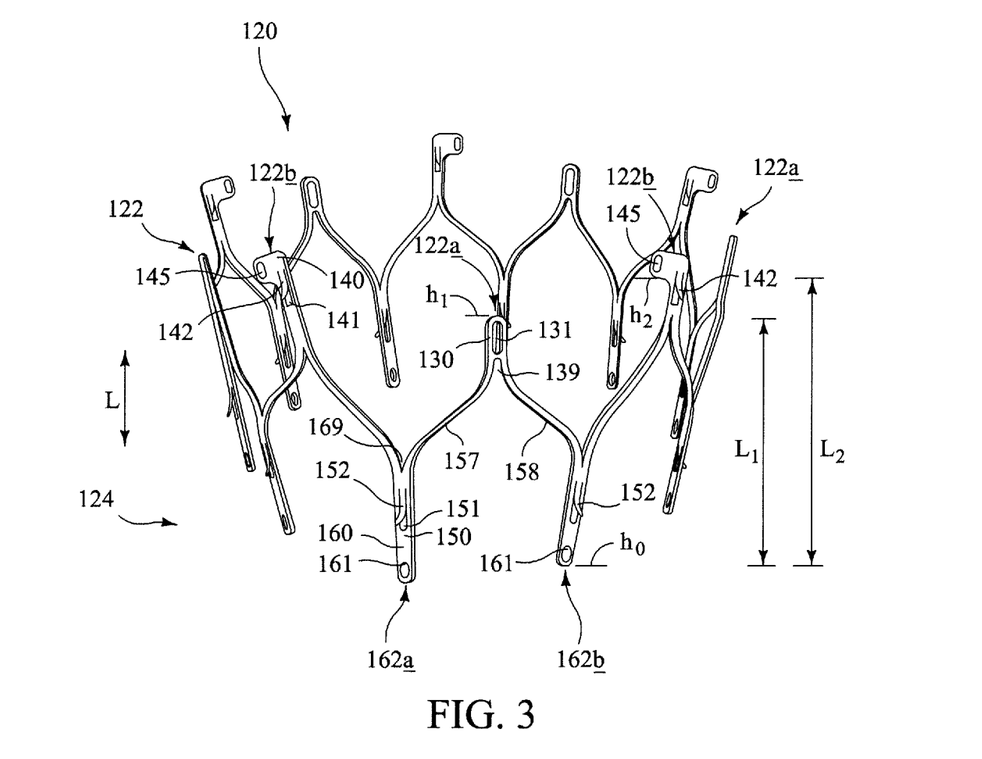
FIG. 3 is an upper perspective view of another exemplary stent.

Referring now to FIGS. 3-6, an alternative stent design is described. In FIG. 3, stent 120 also may be manufactured from a continuous cylinder into which a pattern may be cut by a laser or by chemical etching to produce slits in the wall of the cylinder. The resulting structure may thereafter be heat set to give it a desired final configuration. The preferred final configuration includes a shape having a series of proximal apices and a series of distal apices, as generally shown in FIG. 3. Therefore, the proximal end 122 of the stent 120 may comprise multiple adjacent proximal apices 122a and 122b, while the distal end 124 of the stent 20 may comprise multiple adjacent distal apices 162a and 162b, as shown in FIG. 3.

Figure 4:
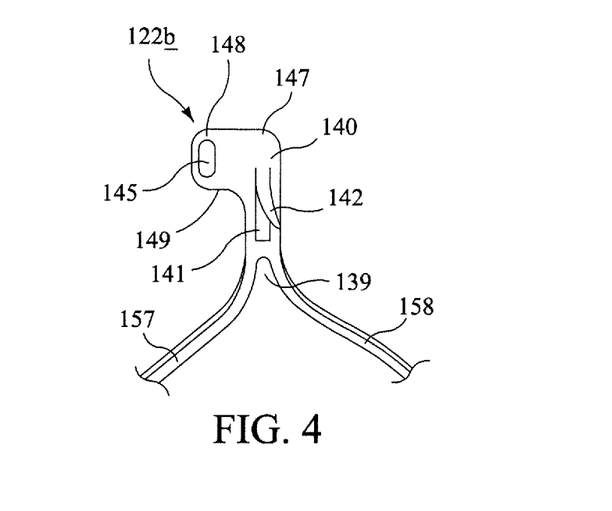
FIG. 4 is a perspective view illustrating features of a proximal apex of the stent of FIG. 3.
Figure 5:
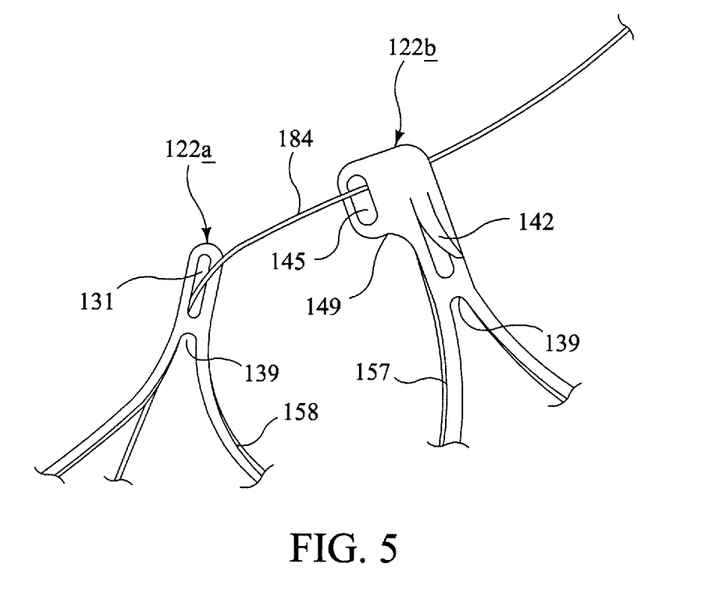
FIG. 5 is a perspective view showing a trigger wire coupled to adjacent proximal apices of the stent of FIGS. 3-4.
Figure 6:
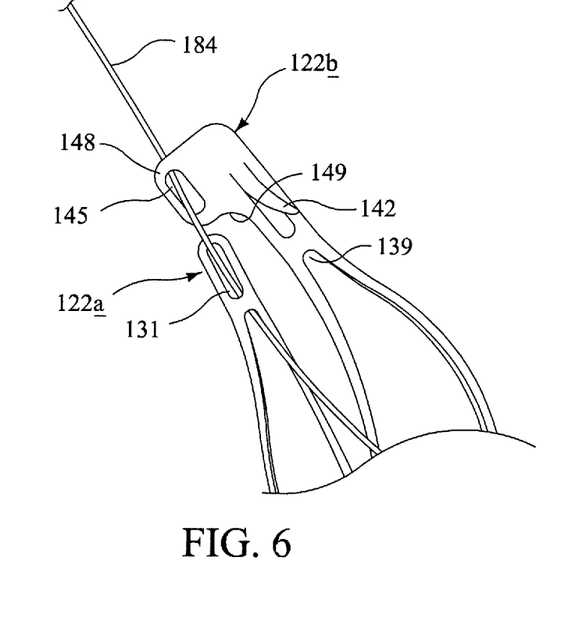
FIG. 6 is a perspective view showing the trigger wire of FIG. 5 holding the stent in a delivery configuration.

One or more pairs of adjacent, proximal apices 122a and 122b may comprise different features. For example, a first proximal apex 122a may comprise an end region 130 having a first bore 131 formed therein, wherein the first bore 131 is configured to receive a trigger wire 184, as shown in FIGS. 5-6 below. A second, adjacent proximal apex 122b comprises an end region 140 having an integral barb 142 formed therein, as shown in FIGS. 3-6. The second proximal apex 122b further comprises a second bore 145 formed therein, as best seen in FIG. 4, which is configured to receive the same trigger wire 184 as the adjacent first proximal apex 122a, as explained and shown with respect to FIGS. 5-6 below. By using adjacent proximal apices 122a and 122b having the different features shown herein, an improved trigger wire attachment may be achieved and barb entanglement may be reduced, as explained further below.

Each of the second proximal apices 122b may comprise first and second regions 147 and 148, as shown in FIG. 4. A single barb 142 may be disposed in each of the second proximal apices 122b generally in the first region 147, while the second bore 145 may be disposed generally in the second region 148, as shown in FIG. 4. The barbs 142 may be formed by laser cutting a desired barb shape into the end regions 140, thereby forming a slit 141, as generally explained with respect to the stent 20 hereinabove. Once the desired barb shape is cut, a main body of the barb 142 may be bent in a radially outward direction and optionally may be sharpened, as generally set forth above.

The second proximal apices 122b further may comprise a recessed portion 149 formed at a location distal to the second bore 145, as best seen in FIG. 4. As will be explained further below, during delivery of the stent 120, the first proximal apex 122a is configured to be pulled towards the second proximal apex 122b and may become nested within the recessed portion 149 of the second proximal apex 122b when a trigger wire is disposed through the first and second bores 131 and 145.

The first bores 131 of the first proximal apices 122a may be disposed slightly distal to the second bores 145 of an adjacent, second proximal apex 122b. Further, a first longitudinal distance L1 between a distal edge h0 of the stent 120 and a proximal edge h1 of each proximal apex 122a may be less than a second longitudinal distance L2 between the distal edge h0 of the stent and a distal edge h2 of each recessed portion 149, as shown in FIG. 3. This length differentiation may facilitate nesting of the first proximal apices 122a within the recessed portions 149 of the second proximal apices 122b during delivery of the stent, as explained further below with respect to FIGS. 5-6.

Referring still to FIG. 3, the stent 120 may comprise at least one strut segment disposed between the proximal and distal apices. In one configuration, the proximal and distal apices are not directly aligned with one another. For example, as shown in FIG. 3, a first angled segment 157 may be disposed between a proximal apex 122a and a corresponding distal apex 162a, and a second angled segment 158 may be disposed between the same proximal apex 122a and an adjacent distal apex 162b. In effect, each proximal apex 122a and 122b extends distally and splits into the first and second angled strut segments 157 and 158, respectively, thereby forming a proximal vertex 139. Similarly, each distal apex 162a and 162b extends proximally and splits into the first and second angled strut segments 157 and 158, respectively, thereby forming a distal vertex 169. In this manner, the stent 120 may be formed into a continuous, generally cylindrical shape, as shown in FIG. 3.

In a compressed state, the first and second angled strut segments 157 and 158 may be compressed such that they are substantially parallel to one another. In the expanded state shown in FIG. 3, the first and second angled strut segments 157 and 158 may be disposed at an angle relative to a longitudinal axis L of the stent 120, as shown in FIG. 3. In the expanded state, the first and second angled strut segments 157 and 158 may be disposed at an angle of about 20-60 degrees relative to the longitudinal axis L of the stent 120. Expansion of the stent 120 is at least partly provided by the angled strut segments 157 and 158, which may be substantially parallel to one another in a compressed state, but may tend to bow outward away from one another in the expanded state shown in FIG. 3. Like the stent 20 noted above, the stent 120 may be formed from any suitable material, and preferably a nickel-titanium alloy, so that it may assume the expanded state shown in FIG. 3 upon removal of a delivery sheath.

The first and second angled strut segments 157 and 158 meet with one another distally to form a distal transition region 150, which effectively is the same as the distal end region 160 of the stent 120. Each end region 160 may be oriented in a direction that is substantially parallel to the longitudinal axis L of the stent 120, as shown in FIG. 3. Further, each end region 160 may comprise a larger surface area relative to the angled segments, since the end regions 160 are composed substantially of multiple different angled segments 157 and 158 meeting up together. At least one distal barb 152 may be formed integrally by laser cutting a desired barb shape, thereby forming a slit 151 into the end region 160, as shown in FIG. 3. Since the end regions 160 may comprise an increased surface area relative to other regions of the stent 120, it may be easier to perforate portions of the end regions 160 without adversely affecting the structural integrity of the stent. Further, a suture bore 161 may be formed in the end regions 160 of each of the distal apices 162a and 162b, as shown in FIG. 3. The distal end 124 of the stent 120 may be coupled to a proximal end of graft material (not shown) by looping the suture through the bore 161 and the graft material, as generally explained above with respect to the embodiment of FIGS. 1-2.

Referring now to FIGS. 5-6, the stent 120 may be delivered to a target site in a compressed configuration using a pushing member, such as pushing member 80 of FIG. 2, and a plurality of trigger wires. In accordance with one aspect, a trigger wire 184 may be looped through the first bore 131 of each first proximal apex 122a, and further looped through the second bore of an adjacent, second proximal apex 122b. Therefore, each individual trigger wire may restrain two separate, adjacent proximal apices during delivery. When the stent 120 is fully compressed, as depicted in FIG. 6, the adjacent first and second proximal apices 122a and 122b may be pulled closer together. Due to the differentiation between lengths L1 and L2, each proximal apex 122a may become nested substantially within the recessed portion 149 distal to the second region 148 of the proximal apex 122b, as shown in FIG. 6. Further, the first bore 131 may be positioned distal to the second bore 145, such that the first and second bores 131 and 145 are disposed substantially in longitudinal alignment with one another when the single trigger wire 184 is disposed through the first and second bores during delivery of the stent.

Advantageously, one single trigger wire may be used to restrain two separate, adjacent apices of the stent 120. Further, the trigger wires 184 are only disposed through the bores 131 and 145, but not disposed around the vertices 139, and therefore the trigger wires may be less likely to become damaged during compression of the stent 120. Further, the stent struts themselves are less likely to become damaged since the trigger wires 184 are isolated within the bores 131 and 145.

Figure 7:
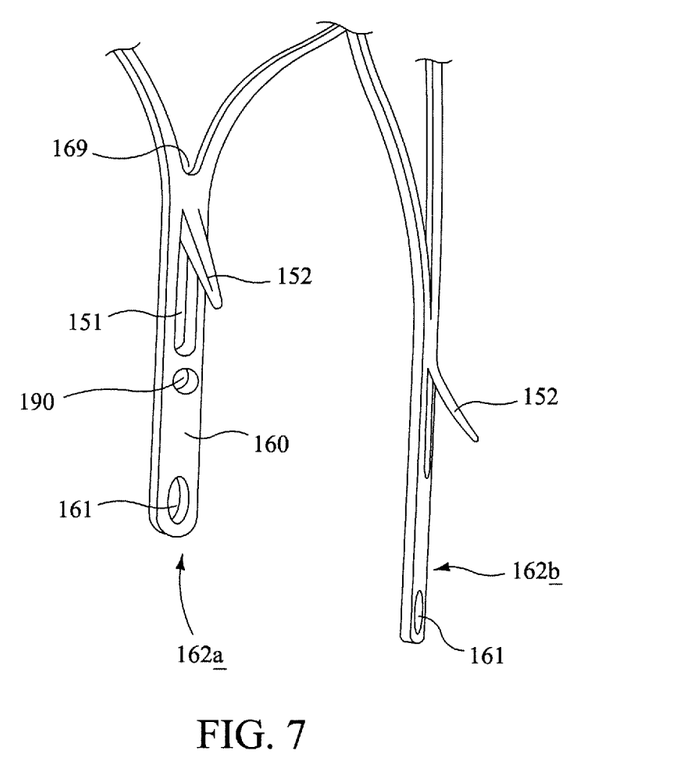
FIG. 7 is a perspective view showing a distal apex having a bore for receiving a radiopaque marker.

Referring now to FIG. 7, one or more of the distal apices 162a and 162b optionally may comprise an imaging bore 190, which may be disposed between the suture bore 161 and the barb slit 151. The imaging bore 190 may receive any suitable radiopaque marker, such as a gold marker. Preferably, the imaging bores 190 and associated radiopaque markers are provided on alternating distal apices, e.g., only distal apices 162a. Alternatively, the imaging bores 190 may be disposed on each distal apex 162a and 162b, or disposed on every third or fourth apex around the perimeter of the stent. The imaging bores 190 may be beveled, or alternatively, may be substantially orthogonal to the strut of the end region 160.

In use, the imaging bores 190 may be aligned with the distal edge of a graft material, for example, when the stent 120 is used for endovascular graft fixation. More specifically, the suture bore 161 overlaps with a proximal region of the graft material, thereby allowing a suture to couple the stent 120 to the graft material with some desired degree of overlap. The proximal edge of the graft material therefore may be aligned with the imaging bores 190. Advantageously, a physician may know exactly where the proximal edge of the graft material is being placed because he or she can view the position of the radiopaque markers in the imaging bores 190. Therefore, the chances of inadvertently overlapping the graft material with a branch vessel, or another undesired location, may be reduced.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis comprising:
   a graft having a first end, a second end, a first edge at the first end, and a second edge at the second end, each of the first and second graft edges at the ends of the graft;
   an expandable stent attached to the graft at one of the ends of the graft, and having a first end, a second end, and a plurality of apices at the second end, each apex having a surface;
   a suture bore disposed through the surface of each of the plurality of apices of the second end of the stent, the suture bore disposed inwardly of an edge of the graft;
   an imaging bore disposed through the surface of each of the plurality of apices of the second end of the stent, the imaging bore disposed directly axially adjacent the suture bore;
   an imaging element disposed in each imaging bore;
   wherein each imaging element is aligned with one of the first and second edges of the graft such that the location of the imaging element corresponds with the edge of the graft with which it is aligned and provides exact imaging of the edge of the graft.

2. The prosthesis of claim 1, wherein the first edge of the graft is a proximal edge of the graft and the second edge of the graft is a distal edge of the graft, and the first stent end is a proximal end of the stent and the second stent end is a distal stent end.

3. The prosthesis of claim 2, where the imaging element is aligned with the proximal edge of the graft.

4. The prosthesis of claim 2, wherein the suture bore is spaced distally of the imaging element.

5. The prosthesis of claim 1, wherein the imaging element is aligned with the first edge of the graft.

6. The prosthesis of claim 1, wherein the imaging element is aligned with the second edge of the graft.

7. The prosthesis of claim 6, wherein the proximal end of the stent extends beyond the proximal end of the graft.

8. A stent-graft comprising:
   a graft having a first end, a second end, a first edge, and a second edge;
   a stent having a first end and a second end, wherein the first end is attached to the graft and adjacent to the first edge of the graft, and wherein the first end comprises a plurality of apices having a bore therethrough;
   a plurality of imaging elements affixed to the stent, such that at least two of the plurality of apices has an imaging element affixed within the bore;
   wherein the plurality of imaging elements is disposed about the perimeter of the stent and are aligned at the first edge of the graft such that the location of the imaging elements corresponds with the first edge thereby providing exact imaging of the first edge of the graft; and
   wherein each apex having an imaging element is sewn to the graft at a point on that apex that is axially separate from the bore and inwardly of the first edge of the graft.

9. The stent graft of claim 8, wherein an imaging element of the plurality of imaging elements is affixed to each of the plurality of apices.

10. The stent graft of claim 8, wherein each of the imaging bores has a luminal opening and an abluminal opening and the imaging elements are disposed within the imaging bores.

11. The stent graft of claim 8, wherein the first edge of the graft is a proximal edge of the graft and the imaging elements are disposed at the proximal edge of the graft.

12. The stent graft of claim 8, wherein the first edge of the graft is a distal edge of the graft and the imaging elements are disposed at the distal edge of the graft.

13. A stent-graft comprising:
   a graft having a first end, a second end, a first edge at the first end of the graft,
   a second edge at the second end of the graft;
   a stent attached to the graft and having a first end and a second end, at least the first end comprising a plurality of apices each having a luminal side and an abluminal side, and having an imaging bore extending through the apices from the luminal side to the abluminal side;
   an imaging element disposed within each of the imaging bores, the imaging element comprising a material having greater visualization under imaging techniques than a material of the stent, and each imaging element being visible from both the luminal side and the abluminal side of the apices;
   wherein each imaging element aligned with an edge of the graft such that the location of the imaging element corresponds with the edge of the graft with which it is aligned thereby providing exact imaging of the edge;
   wherein each apex is sewn to the graft at a point on the apex axially separate from the bore and inwardly of the first edge of the graft.

14. The stent graft of claim 13, wherein the imaging elements is are disposed at the proximal edge of the graft.

15. The stent graft of claim 13, wherein the imaging elements is are disposed at the distal edge of the graft.

16. The stent graft of claim 13, further comprising an attachment bore in each of the apices adjacent to the imaging bore.

17. The stent graft of claim 16, where the attachment bores are disposed inwardly of an edge of the graft.

* * * * *